US012751616B2

(12) United States Patent
Yates et al.

(10) Patent No.: US 12,751,616 B2
(45) Date of Patent: Oct. 6, 2026

(54) FUNDUS IMAGING APPARATUS AND METHODS

(71) Applicant: Retivue, LLC, Charlottesville, VA (US)

(72) Inventors: Paul Andrew Yates, Charlottesville, VA (US); Viatcheslav Orlov, Henrico, VA (US)

(73) Assignee: RETIVUE, LLC, Charlottesville, VA (US)

(*) Notice: Subject to any disclaimer, the term of this patent is extended or adjusted under 35 U.S.C. 154(b) by 994 days.

(21) Appl. No.: 17/659,597

(22) Filed: Apr. 18, 2022

(65) Prior Publication Data

US 2022/0330817 A1 Oct. 20, 2022

Related U.S. Application Data

(60) Provisional application No. 63/175,876, filed on Apr. 16, 2021.

(51) Int. Cl.
*A61B 3/12* (2006.01)
*A61B 3/14* (2006.01)

(52) U.S. Cl.
CPC .............. *A61B 3/1208* (2013.01); *A61B 3/14* (2013.01)

(58) Field of Classification Search
CPC ............ A61F 9/008; A61F 2009/00846; A61F 2009/00851; A61F 9/007; A61F 2009/0087; A61B 3/14; A61B 3/102; A61B 3/0025; A61B 3/0058; A61B 17/0231; A61B 3/0008; A61B 3/12; A61B 2017/00725; A61B 3/13; A61B 18/20; A61K 9/0051; A61K 9/0048; G02B 2027/0118; G02B 2027/0138; G02B 2027/014
See application file for complete search history.

(56) References Cited

FOREIGN PATENT DOCUMENTS

WO WO 2020093060 * 5/2020 ......... A61F 9/00821

OTHER PUBLICATIONS

Welch Allyn Patient Eyecup; https://a.co/d/00xa3L4; provided May 5, 2023; product existed prior to Apr. 16, 2021.
Surtex Instruments; Alphonso Infant Lid Speculum; https://surtex-instruments.com/product/alphonso-infant-lid-speculum/; 2020.
Surtex Instruments; Cooke Eye Speculum; https://surtex-instruments.com/product/cook-eye-speculum/; 2020.
Surtex Instruments; Frankel Infant Lid Speculum; https://surtex-instruments.com/product/frankel-infant-lid-speculum/; 2020.
Serfinity; Integra Lifesciences—Eye Lid Speculum Sauer 1 inch L-18-3; ) https://serfinitymedical.com/products/kcm23-integra-lifesciences-eye-lid-speculum-sauer-1-inch-I-18-3-679201?variant=39941708120139&gad=1&gclid=Cj0KCQjw6cKiBhD5ARIsAKXUdyZUWdwi1973tCyluZeWutSNOKys9ohcfIUTWj5eRUyKu8RD1c7Bh9AaAl4tEALw_wcB; provided May 5, 2023; product existed prior Apr. 16, 2021.
Welch Allyn; PanOptic Ophthalmoscope and iExaminer System; Welch Allyn PanOptic Plus Ophthalmoscope | Welch Allyn | Hillrom; 2016.

* cited by examiner

*Primary Examiner* — Brandi N Thomas
(74) *Attorney, Agent, or Firm* — Simpson & Simpson, PLLC; Jeffrey B. Powers

(57) ABSTRACT

Speculums and spacers are used to position a retinal camera to obtain images of a fundus of an eye. In some instances, the speculums and spacers are designed to contact the eye to prevent rotation of the eye during imaging. In other instances, no contact is made with the eye. A light source may include visible light or limited to infrared light.

4 Claims, 11 Drawing Sheets

FUNDUS IMAGING APPARATUS AND METHODS

CROSS-REFERENCE TO RELATED APPLICATION

The present application claims priority of U.S. Provisional Patent Application Ser. No. 63/175,876, titled RETINAL CAMERA-SPACER AND SPECULUM and having a filing date of Apr. 16, 2021, which is hereby incorporated by reference herein, in its entirety.

STATEMENT REGARDING FEDERALLY SPONSORED RESEARCH

This invention was made with government support under Contract No. 5 R44 EY023505-05 PI awarded by the National Institutes of Health. The United States Government has certain rights in the invention.

BACKGROUND

Imaging a fundus of an eye (including the eye's retina) for diagnostic purposes has proved a difficult task due to the precision required when aligning the camera with the eye to obtain an optimal photo. With traditional 45-degree field of view fundus photography, the requirement is generally to hold the camera approximately 20 mm or more away from the eye with the camera centered on the pupil. Positioning tolerances range on the order of +/−5 mm in the x, y, and z axes. Failure to align the camera properly will result in suboptimal illumination of the fundus, shadowing by the iris into the image, and entrance of purkinje haze into the final composed image.

The majority of portable fundus cameras have a handle with a trigger button and a user holds the camera in front of the eye, using on-screen alignment guides to center the front of the camera with the eye. These guides can consist of purkinje reflections, general retinal reflectance, or secondary optics or illumination to manually or automatically judge camera position with respect to the center of the pupil. In some instances, xyz position of the camera is automatically adjusted internally to align with the eye from an initial starting coarse alignment. This has greatly improved the reliability of handheld retinal photography.

Nevertheless, without a fixed pivot point on the end of the camera close to the eye, even the act of pressing the camera trigger, can cause camera misalignment, as it results in small motion of the camera relative to the eye. Thus, more recent commercial cameras will, when judging correct position of camera to eye, take the photo automatically without requiring manual triggering. This still leaves the initial task of getting the camera anywhere close to the eye, and more importantly maintaining that position, often a freeform effort. It is the primary difficulty most novice users encounter when first learning handheld retinal photography.

Alignment of a portable camera can be greatly simplified by having a fulcrum at the front of the camera to provide stability of camera position and finer positioning than can be achieved by slight adjustments of the front of the camera relative to the eye. In some instances this fulcrum is achieved by gripping the camera with one's thumb and index finger and stabilizing against the patient's forehead by use of one's pinky. This hand can then guide the camera to the eye and make fine adjustment in the x, y, and z axis to center the camera with the pupil at the correct working distance from the eye. It is a highly trainable and feasible task, but it still has the disadvantage of requiring direct patient contact, even though in theory portable fundus photography can be accomplished without requiring contact with the eye. This approach has been iterated upon by placing a compressible rod on the portable camera that is placed against the forehead to again quickly establish a rough working distance from the eye.

An alternative approach is to attach an eye cup or bellows around the front camera lens. The eye cup/bellows rests along the forehead and cheek bone and also serves to stabilize the front of the camera relative to the eye. The added benefit of an eye cup is the ability to shield outside light from the eye, which can aid in non-mydriatic retinal photography. Such eye cups can take several forms, with a resemblance closer in size and appearance to a pirate patch attached to the front of the camera, or a rounder accordion type ring (bellows) attached to the camera. The purpose of these assistive devices attached to the camera are to 1) place the portable fundus camera at approximately the 20 mm working distance from the eye for optimal photography 2) block stray light from entering the eye to improve image quality 3) have some compressible and/or flexible qualities to allow finer adjustment in x, y, z positioning of the front of the camera relative to the eye from the initial positioning.

A key disadvantage of the eye cup approach is that by blocking view of the eye, it can still be difficult to judge externally, centration of camera with respect to eye. The other disadvantage is that at the requisite 20 mm working distance from the eye for a typical 45 degree fundus camera, the precision of camera placement offered by these devices is no better than 2 mm or more along any axis of movement. The reason is that enough material flexibility in stretch and tensile strength must be offered given significant variations in brow prominence that it is less capable of sub-millimeter adjustments. However, for 45-degree field of view photography the 2 mm positioning tolerance meets acceptable performance criteria to accomplish the task at hand.

For wider field of view photography, particularly greater than 60-degree (i.e., widefield of view imaging) of the retina, this fulcrum issue must be solved in an entirely different manner. Imaging a wider field of view of the retina typically requires much closer working distances of the camera to the eye, often in the 2 to 10 mm range. The greatest application for this technology has been in imaging premature babies for retinopathy of prematurity. To achieve stability and provide a fulcrum for the camera, existing commercial devices have the primary lens on the device directly contact the cornea of the eye. Pressing down on the cornea with the camera device holds the eye in place and allows a surface that provides resistance when tilting the device to image more peripheral aspects of the retina. This approach completely eliminates eye movement and allows the camera user to quickly and easily adjust the camera to the correct z position from the eye, since the contact of eye with camera is by definition at the correct z distance. Further, the cornea offers the camera resistance when tilting the device relative to the central visual axis.

However, there are several distinct disadvantages to this approach. First, use of a contact lens on the front of the imaging camera requires a gel substrate between camera lens and eye which can be the source of significant light scattering and aberrations. Second, pressing with the camera contact lens on the cornea of the eye can potentially cause damage to the eye, and has issues of sterility when the camera is used on multiple babies. Third, pressing on the cornea with the camera contact lens introduces corneal striae which can cause light scattering and artifacts in the recorded image of the eye. Fourth, the act of placing the eye on the cornea is not easily performed by untrained operators given the size of the cornea and the required feedback to know when one is pressing too hard or too lightly on the eye.

Non-contact widefield retinal photography of babies offers the possibility of overcoming the sterility and imaging artifact issues associated with contact widefield photographic approaches. The problem is that with working distances in the 1-10 mm range, and optimal positioning tolerances less than 1 mm, freehand positioning of the device relative to the baby eye is extremely difficult. This potentially limits the feasible application of this approach. This difficulty is amplified when trying to tilt the camera relative to the eye to image the retinal periphery where retinopathy of prematurity is often found. There is no fulcrum to stabilize the front of the widefield camera against because there is no contact with the eye to offer the necessary friction. It is extremely difficult to repeatedly tilt the camera and end up at the correct position and requisite z distance from the eye. Yet, in order to perform the necessary edge-to-edge imaging of the eye, such tilt images are required for up to 15 images per eye. This makes non-contact imaging for all intents and purposes impractical on babies. In general, babies' eyes move, and their tolerance to long photographic sessions is time-limited, requiring an entire imaging session to ideally be complete within a few minutes or less. For this reason non-contact widefield imaging of the eye has not been a suitable replacement for contact based widefield screening of babies' eyes.

SUMMARY

There remain several problems to solve in the use of non-contact widefield cameras to provide imaging of babies eyes: 1) placement of the camera at the requisite z-distance from the eye with less than +/−1 mm tolerance in a reliable and repeatable manner 2) allowing the camera to be placed in a position not along the central visual axis at a precise z-distance within +/−1 mm tolerance for the purpose of imaging the retinal periphery 3) avoiding a need for direct contact with the cornea of the eye which can cause imaging aberrations 4) allowing for tilt of the camera relative to the eye without requiring complete repositioning of the camera 5) providing for fixation of the baby eye without requiring camera contact with the cornea of the eye, so that the eye can be imaged without movement. Envisioned solutions to these imaging requirements are the focus of the present subject matter.

An aspect of the invention is directed to a camera spacer for use with a non-contact, widefield camera having an optical axis. The camera spacer defines an operating distance of the camera relative to the eye along the optical axis. The spacer comprises a spacer body having an aperture extending therethrough and a longitudinal axis extending through the aperture to be nominally aligned with the optical axis when the camera is operatively positioned relative to the camera spacer. The aperture has a diameter of 8 mm-25 mm. The spacer body has a first surface and an opposing second surface, each extending generally transverse to the longitudinal axis. The camera spacer further comprises a contact ring extending from the first side of the spacer body and surrounding the aperture; the contact ring has a contact surface at a distal end. The camera spacer further comprises a sidewall extending from the second side of the spacer body, the sidewall having an inner surface defining a receptacle for receiving a portion of the camera when the camera is positioned such that the optical axis is aligned with the longitudinal axis. The spacer body, contact ring, and the sidewall are constructed of a semirigid material. To accommodate cameras having different working distances, different camera spacers may have lengths from the contact surface to the second surface in the direction of the longitudinal axis of 0.5 to 10 mm. As a result of the above design, when the camera spacer is operatively positioned relative to the eye and the camera is positioned to contact the second surface, the camera is located at a suitable operating distance from the cornea of the eye and the sidewall flexibly resists tilting of the camera relative to the longitudinal axis.

It will be appreciated that the contact surface may contact a lid speculum as set forth herein or directly contact the sclera of the eye facilitating non-contact use of a camera. The semirigid material allows the sidewall to stretch as a camera located in the receptacle is tilted, thereby providing tactile feedback to a camera operator. In some embodiments, the outer diameter of the camera spacer, measured transverse to the longitudinal axis is less than 30 mm to fit in a baby eye (overall device size)

It will be appreciated that downward force from the camera through the contact ring to the lid speculum or from contact ring to the sclera of the eye potentially fixates the eye in position. It will also be appreciated that the semirigid material provides friction between contact ring and lid speculum (or extension ring and sclera of eye) that is sufficient to prevent movement of the camera relative to the lid spectrum or the sclera under operative forces.

Another aspect of the invention is directed to an eye lid speculum to retract eye lids of a patient's eye for use with a non-contact, widefield camera, the speculum comprising a first arm and a second arm coupled at a vertex about which the first arm and the second arm, each of the arms having a corresponding blade extending along a length of the arm to engage and retract an upper and lower eye lid, respectively, the lengths moving circumferentially about the vertex in a plane, and each blade having an eye lid engagement surface. Each arm has a thickness extending perpendicular the plane and measured from an upper-most portion of the engagement surface to an arm upper surface that is greater than 2 mm (and typically less than 8 mm) and, along the length, the arm upper surface having a width in the plane greater than 2 mm (and typically less than 5 mm) to support the non-contact camera. A speculum may be configured such that retraction is controlled by a spring or a thumb screw.

A further aspect of the invention is directed to an eye lid speculum to retract eye lids of a patient's eye for use with a non-contact, widefield camera, the speculum comprising a first arm and a second arm coupled at a vertex, each of the arms having a corresponding blade extending therefrom to engage and retract an upper and lower eye lid, respectively, and each blade having an eye lid engagement surface. Each arm has a portion extending further from the vertex than its corresponding blade to support the non-contact camera.

In some embodiments, the portion of first arm that extends beyond the blade is curved toward the second arm, and the portion of the second arm that extends beyond the blade is curved toward the first arm.

A still further aspect of the invention is directed to an eye lid speculum to retract eye lids of a patient's eye for use with a non-contact, widefield camera, the speculum comprising a first arm and a second arm coupled at a vertex. Each of the arms has a blade extending therefrom to engage and retract a corresponding eyelid. Each blade has a lead, end surface disposed to extend under the corresponding eyelid. The lead, end surfaces move circumferentially about the vertex within an end-surface plane, and each lead end surface has a normal that extends transverse to the end-surface plane.

In some embodiments the arm length measured from the vertex is less than 40 mm (and typically greater than 30 mm) to fit baby eye. In some embodiments, the maximum blade spread (when not in the eye) is less than 35 mm to fit a baby eye and in the eye is less than 20 mm. Maximum blade spread is measured at the location of maximus separation of the blades.

Yet another aspect of the invention is directed to a kit for use with a non-contact, widefield camera having an optical axis, comprising a speculum comprising a first arm having a first blade with a first tip and a second arm having a second blade with a second tip. The first arm and the second arm are coupled at a vertex. The first blade and the second blade are configured to retract an upper and lower eye lid of a patient's eye, respectively.

The kit further comprises a camera spacer, comprising an aperture extending therethrough. The aperture is substantially centered about a longitudinal axis extending through the aperture to be nominally aligned with the optical axis when the camera is operatively positioned relative the camera spacer. The aperture has a diameter of 8 mm-25 mm. The camera spacer further comprises a contact ring surrounding the aperture and substantially concentric with the aperture about the longitudinal axis. The contact ring has a contact surface at a distal end. The camera spacer further comprises a receptacle for receiving a portion of the camera. The receptacle terminates at a surface including the aperture. The surface surrounds the longitudinal axis such that, when the camera contacts the surface, the optical axis can be aligned with the longitudinal axis. The spacer is constructed of a semirigid material. In use, when the speculum is operatively positioned relative to the eye and the contact surface is positioned on (i.) the first arm and the second arm or (ii.) the first blade and the second blade, lengths from each of the first tip of the first blade and the second tip of the second blade to the surface, in the direction of the longitudinal axis, are 1 to 10 mm.

In use, when the camera is positioned to contact the second surface, the camera is located at a suitable operating distance from the cornea of the eye and the sidewall flexibly resists tilting of the camera relative to the longitudinal axis, thereby providing tactile feedback to a user of the camera.

Another aspect of the invention is directed to a method of positioning a non-contact, widefield camera having an optical axis relative to an eye, the method comprising positioning a spacer relative to the eye. The spacer having an aperture extending therethrough and a longitudinal axis extending through the aperture. The spacer has a receptacle. The receptacle terminates at a surface surround the longitudinal axis. The spacer is constructed of a semirigid material. After the spacer is positioned relative to the eye, the camera is arranged in the receptacle such that the camera contacts the surface and the longitudinal axis is substantially aligned with the optical axis. The camera is located 1 to 10 mm from a surface of the eye in the direction of the longitudinal axis.

In some instances, the spacer further comprises a contact ring surrounding the aperture and concentric with the aperture about the longitudinal axis; and the contact ring has a contact surface at a distal end; and the method further comprises retracting an upper and lower eye lid of a patient's eye a speculum using a first blade and a second blade, respectively, with the first blade extending from a first arm of the speculum and the second blade extending from a second arm of the speculum. And the step of positioning the spacer further comprises locating the contact surface on (i.) the first arm and the second arm or (ii.) the first blade and the second blade.

For example, in use, when the speculum is operatively positioned relative to the eye and the contact surface is positioned on (i.) the first arm and the second arm or (ii.) the first blade and the second blade, lengths from each of the first tip of the first blade and the second tip of the second blade to the surface, in the direction of the longitudinal axis, are 1 to 10 mm.

In some instances, the aperture is nominally aligned with the optical axis when the camera is operatively positioned relative the camera spacer. In some instances, the aperture having a diameter of 8 mm-25 mm. In some instances, when the camera contacts the surface, the optical axis is aligned with the longitudinal axis.

In some instances, a kit can be constructed such that the lid speculum may be configured to receive the non-contact widefield camera without requirement for the spacer between the lid speculum and the widefield camera. In such instances the non-contact widefield camera lens housing will be configured to ideally be directly received and in direct apposition to the lid speculum. For example, the contour of said non-contact widefield camera lens housing will conform to the contour of said lid speculum arms and thereby ideally support the non-contact widefield camera to provide an ideal fulcrum and alignment of said camera with said lid speculum. The contoured surface of said lid speculum can be aligned with the center axis of said eye to allow for quick centration of said non-contact widefield camera with said eye by placing said non-contact widefield camera lens housing onto said lid speculum where the contour of lid speculum and lens housing conform. The contoured surface can further place the camera lens housing at the correct tilt relative to said eye by means of alignment with said lid speculum which will have tilt alignment with said eye due to its anatomical positioning on the eyelid of said eye being imaged.

The lid speculum arms may be at a greater distance from said eye to be imaged than the required position of said camera lens of said non-contact widefield camera. For instance, for most babies, the top of the lid speculum arm is 2 mm from the apex of the corneal surface of said baby eye. Yet, the camera lens may require for optimal imaging a distance of 1 mm from said apex of said corneal surface of said baby eye. In these instances, the peripheral aspect of said non-contact widefield camera lens housing can contour to said lid speculum, while the central portion of said non-contact widefield camera lens housing and lens protrudes between said upper and said lower arm of the lid speculum to allow positioning closer than 2 mm to said baby eye.

For instance, said peripheral aspect of said non-contact widefield camera lens housing can be flat to rest on said flat lower and flat upper arm of said lid speculum to achieve ideal apposition of said non-contact widefield camera to said lid speculum. Said central portion of said non-contact widefield camera lens housing protrudes between said upper and lower arm of said lid speculum, with positioning of said upper and lower arms of said lid speculum providing centration of said non-contact widefield camera relative to the apex of the cornea of said baby eye.

Aspects of the speculum-camera example can be also applied to a camera spacer sitting on said lid speculum or directly on said baby eye, with the camera spacer conforming to said lid speculum or the eye, and said non-contact widefield camera lens housing conforming to the camera spacer. Such conformation allows alignment of said non-contact widefield camera with said baby eye as a result of the camera spacer or said lid speculum or the combination of the camera spacer and the lid speculum initial alignment with said baby eye.

It will be appreciated that the longitudinal distance of the non-contact widefield camera from the eye can be adjusted with precision be altering the longitudinal thickness of the lid speculum arms, the longitudinal thickness of the camera spacer or the longitudinal thickness of the non-contact widefield camera lens housing.

It will also be appreciated that just as conformation of the camera spacer, the lid speculum, or said non-contact widefield camera lens housing along a tangential axis can allow for precise longitudinal positioning, conformation of the camera spacer side wall with said camera lens housing side wall can allow for precise positioning by controlling tilt of the non-contact widefield camera relative to the eye to be imaged.

Further aspects of the invention are directed to a kit for use in imaging a fundus of an eye, comprising (A.) a speculum comprising a first arm having a first blade and a second arm having a second blade, the first arm and the second arm coupled at a vertex, the first blade and the second blade configured to retract an upper and lower eye lid of the eye, respectively, and (B.) a fundus camera comprising imaging optics and a housing, the housing containing the imaging optics and having an outer surface. Accordingly, when the speculum is operatively positioned relative to the eye, the camera is positioned by an interface formed with the outer surface, to maintain the camera at a fixed distance relative to (i.) the first arm and the second arm or (ii.) the first blade and the second blade such that the fundus camera is operatively positioned to image a fundus of an eye.

In some embodiments, the interface is formed by the outer surface and (i.) the first arm and the second arm or (ii.) the first blade and the second blade. The interface may be a lock and key interface.

In some embodiments, the kit further comprises (C.) a camera spacer, comprising I. a spacer body having a first surface and an opposing second surface, the body having an aperture extending therethrough, the aperture substantially centered about a longitudinal axis of the spacer, the aperture having a diameter of 8 mm-25 mm, II. a contact ring having a contact surface at a distal end of the ring to contact the (i.) the first arm and the second arm or (i.) the first blade and the second blade, and III. a receptacle formed by a sidewall extending from the spacer body, for receiving a portion of the camera, the receptacle terminating at an end surface including the aperture. The end surface is disposed such that, when the contact surface contacts the (i.) the first arm and the second arm or (i.) the first blade and the second blade, and the interface is formed by the sidewall and the outer surface of the camera, the optical axis is aligned with the longitudinal axis and the fundus camera is operatively positioned to image a fundus of an eye. The interface may be a lock and key interface.

In some embodiments, the camera comprises an objective lens having a concave first surface. The spacer may be constructed of a semirigid material.

Another aspect of the invention is directed to a fundus camera comprising imaging optics having an optical axis, and a housing, the housing enclosing the imaging optics and having an outer surface containing at least one step that extends transverse to the optic axis.

In some embodiments, the step extends substantially perpendicular to the optical axis. In some embodiments, the step constitutes a portion of an interface capable of forming a lock and key interface.

Another aspect of the invention is directed to a method of positioning a non-contact, widefield camera having an optical axis relative to an eye. The method comprises retracting an upper and lower eye lid of a patient's eye using a first blade and a second blade of a speculum, respectively, the first blade extending from a first arm of the speculum and the second blade extending from a second arm of the speculum, and fixing a distance of the camera relative to (i.) the first arm and the second arm or (ii.) the first blade and the second blade. Accordingly, the camera is operatively positioned to image a fundus of the eye without contacting the eye.

In some instances, the step of fixing the distance comprises contacting (i.) the first arm and the second arm or (ii.) the first blade and the second blade with the camera to form an interface between an outer surface of the camera and the speculum.

In some instances, the outer surface comprises at least one step and the interface is formed between the step and the speculum. The interface may be a lock and key interface.

In some instances, the step of fixing the distance comprises positioning a spacer on (i.) the first arm and the second arm or (ii.) the first blade and the second blade, the spacer having an aperture extending therethrough and a longitudinal axis extending through the aperture, and the spacer having a receptacle, the receptacle terminating at an end surface surrounding the longitudinal axis. Then, after the spacer is positioned, the camera is arranged in the receptacle such that the spacer and the outer surface of the camera form an interface and the longitudinal axis is aligned with the optical axis.

In some instances, the outer surface comprises at least one step and the interface is formed between the step and the spacer. The interface may be a lock and key interface.

In some instances, the camera located 1 to 10 mm from a surface of the eye in the direction of the longitudinal axis.

The spacer is constructed of a semirigid material. In some instances, the camera comprises an objective lens having a concave first surface.

The terms "retinal camera" and "retinal imaging" are used generally to refer to a camera capable of imaging the back of the eye; accordingly, a retinal camera is commonly used to image the entire fundus of an eye, and the terms retina and fundus are used interchangeably herein when referring to imaging of the back of the eye.

As used herein, the term "wide field camera" means a camera suitable for imaging greater than 60 degrees (+/−30 degrees) relative to the optical axis of the eye. Although the invention is described above for use with a wide field camera, any suitable retinal camera may be used.

As used herein, the term "non-contact camera" refers to a camera designed to be operated without any part of the camera in direct contact with the eye. It will be appreciated that a non-contact camera may have advantages related to health regulations and sterilization requirements.

As described herein, a non-contact camera may be in contact with one or more implements (e.g., a speculum or a camera spacer) which, in turn, directly contact the eye.

As used herein, the term "semirigid material" refers to a material that does not deform under ordinary gravity forces, but does flex when subjected to ordinary forces of retinal photography. A semirigid material as defined herein has a shore hardness value in the range 20 A-70 A or in the range 40 A-60 A; in one embodiment the material has a shore hardness value of 50 A. For example, a silicone, a rubber or a suitable acrylic may be semi-rigid.

The term "upper" when referring to a medical device refers to a portion of the device relatively further from an eye when the device is in use.

DETAILED DESCRIPTION

It is envisioned that fixation and rapid precision positioning and tilt of a camera relative to a baby's eye without requiring direct contact of the camera with the cornea of the eye can be accomplished through several mechanisms, for example using a camera spacer and/or an eyelid speculum (also referred to herein as an lid speculum or simply as a speculum).

Figures 1A, 1B, 1C, 1D:
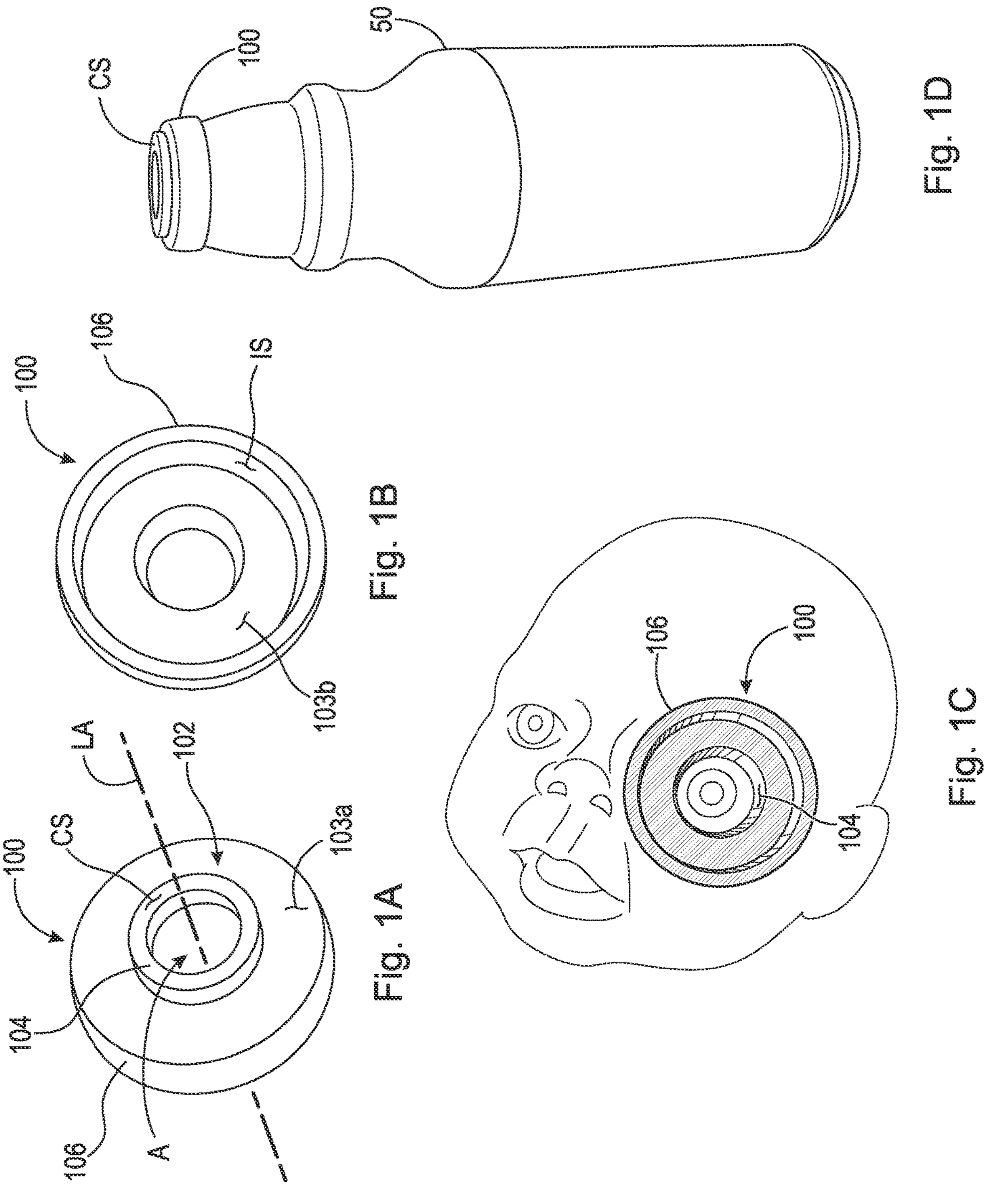
FIGS. 1A-1B are illustrations of an example of an embodiment of a spacer according to aspects of the present invention.
FIG. 1C illustrates the spacer as in FIGS. 1A and 1B disposed on a baby's eye.
FIG. 1D illustrates the spacer as in FIGS. 1A and 1B having a camera located in a receptacle of the spacer.

FIGS. 1A-1B are illustrations of an example of an embodiment of a camera spacer 100 according to aspects of the present invention. As discussed in greater detail below, the camera spacer defines an operating distance of a camera 50 relative to an eye along an optical axis of a camera. The spacer comprises a spacer body 102 having an aperture A extending therethrough and a longitudinal axis LA extending through the aperture to be nominally aligned with the optical axis of the camera when the camera is operatively positioned relative to the camera spacer. Aperture A has a diameter of 8 mm-25 mm. The spacer body has a first surface 103*a* and an opposing second surface 103*b*, each extending generally transverse to the longitudinal axis. The camera spacer further comprises a contact ring 104 extending from the first side of the spacer body and surrounding the aperture. The contact ring has a contact surface CS at a distal end. The camera spacer further comprises a sidewall 106 extending from the second side of the spacer body. The sidewall has an inner surface IS defining a receptacle for receiving a portion of the camera when the camera is positioned such that the optical axis is aligned with the longitudinal axis. For example, for a spacer having a Shore A hardness of 50, the sidewall may define a receptacle depth (from the spacer body) about 2 mm to about 10 mm. The wall having a thickness of about 2 mm thick. The contact ring having a thickness of about 0.5 mm to about 1.5 mm, depending on whether the contact surface is to contact the eye directly or to rest on a speculum (as set forth below).

In some embodiments, contact ring 104 (including contact surface CS) is made of a semirigid material with a flexible interface (i.e., contact surface CS) for contacting a sclera of a baby's eye. It is additionally envisioned that the contact ring is made of a material that is easily sterilized to allow for repeat use. In some embodiments, the spacer including contact ring 104 and sidewall 106 are made of a semirigid material such as silicone. In some embodiments, the entire spacer is made of the semirigid material.

FIG. 1C illustrates the contact ring of the spacer located on a sclera of a baby's eye. The camera spacer 100 is fashioned such that, when the camera is in the receptacle with the end of the camera contacting second surface 103*b* (i.e., the end surface of the receptacle) and contact surface CS is applied to the white sclera, the front imaging surface of the camera 50 is at the requisite z-distance from the eye. The camera, upon contact of the sclera with the contact ring 104, can be retropulsed (i.e., pressed) towards the baby eye to hold the eye in place, essentially freezing movement of the eye. The placement of pressure on the sclera avoids the need for lubricating gel and induction of corneal striae that are evident with prior widefield cameras that directly contact the cornea of the eye. The contact ring 104 also provides a fulcrum against which tilt of the camera relative to the eye can be accomplished. The use of silicone or another flexible material (e.g., a semirigid material as defined herein) on the contacting surface of the contact ring 104 allows the surface tension of the device relative to the pressure it exerts on the eye to be spread out across a relatively large surface area.

The contact ring when placed directly on the baby eye may contact the sclera at discrete fixation points, or may accomplish fixation through use of continuous 360° contact with the sclera by the contact ring.

As shown in FIG. 1D, camera 50 can be located in the receptacle of the spacer such that spacer 100 is secured to the front of a non-contact camera 50. In some embodiments, the camera and spacer are sized and shaped to provide a press-fit such that the spacer can be removably positioned around the front of camera 50. In some embodiments, the contour of the spacer and the camera form an interface and, in some embodiments, have a more complex surface where the interface is a lock-and-key interface.

The semirigid side wall 106 interface of the spacer 100 allows the camera to offer appropriate resistance to tilt of the camera relative to the eye, improving the rate at which accurate peripheral imaging can be accomplished. Repositioning of the camera can be accomplished by sliding the contact surface CS slightly along the scleral surface and/or tilting the camera relative to the central axis of the eye. The semirigid material allows the contact ring 104 and side wall 106 to resist the tilt and thereby offer higher precision control of the tilt. In one embodiment, it is envisioned that there is compressibility of this flexible material in the z-axis of camera movement to allow for further fine positioning of the camera along the z-axis relative to the eye.

Figure 2A:
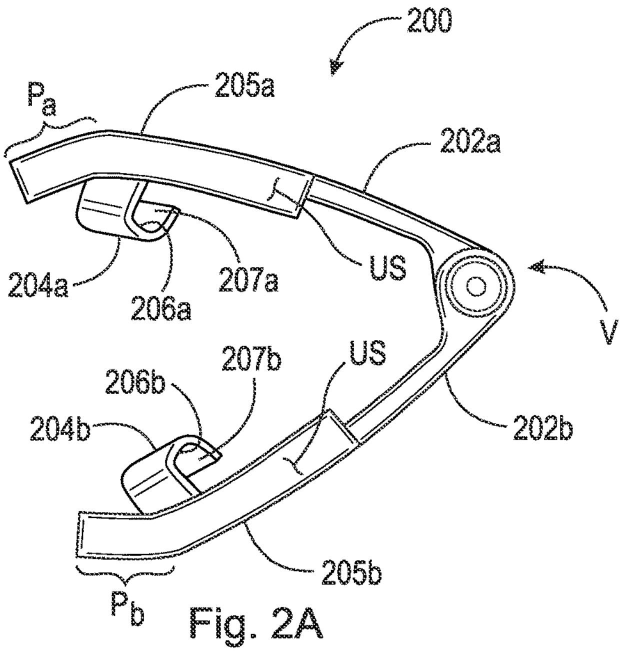
FIGS. 2A-2C illustrate a top view, a bottom view, and a side view of an example of an embodiment of a speculum according to aspects of the preset invention.
Figure 2B:
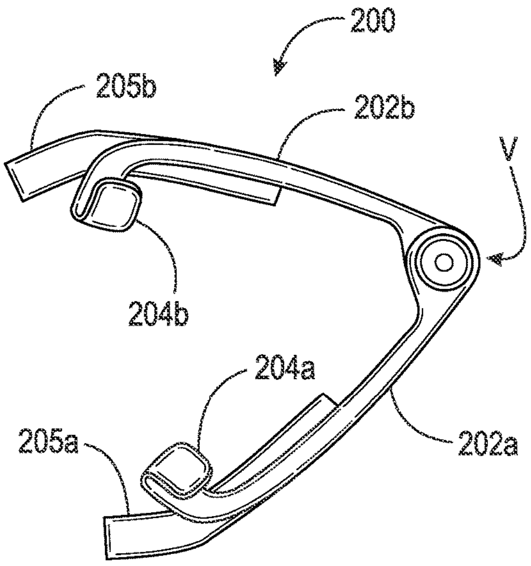
Figure 2C:
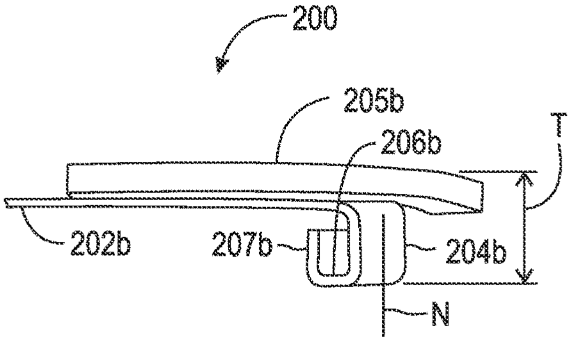
Figure 2D:
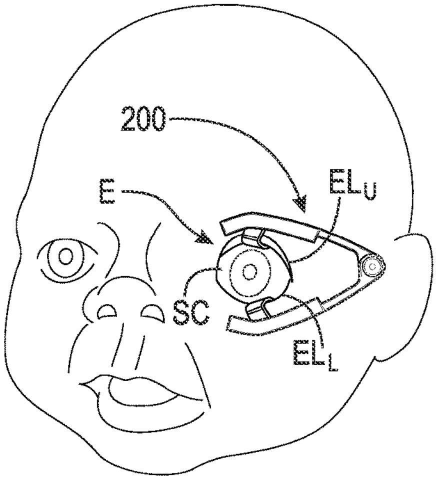
FIG. 2D illustrates a speculum disposed to retract the eyelids of a baby.

FIGS. 2A-2C illustrate a top view, a bottom view, and a side view of an example of an embodiment of a speculum 200 according to aspects of the present invention. Such a speculum is capable of solving at least some of the aforementioned problems of using a non-contact camera. Speculum 200 comprises a first arm 202*a* having a first blade 204*a* and a second arm 202*b* having a second blade 204*b*, the first arm and the second arm coupled at a vertex V; and the arms move circumferentially about the vertex in a plane. In the illustrated embodiment, the plane is parallel to the plane of the sheet on which the speculum is illustrated in FIGS. 2A and 2B. As shown in FIG. 2D, the first blade and the second blade are configured to retract an upper eye lid $EL_U$ and lower eye lid ELL of a baby's eye E. Each blade has a corresponding eye lid engagement surface 206*a*, 206*b*.

Speculum 200 is sized such that, when the lid speculum is pressed towards eye E or the orbit containing the eye, the speculum blades 204*a*, 204*b* contact the sclera SC of the eye. In this manner blades 204*a* and 204*b* can hold the eye in place to prevent movement (i.e., rotation) of said eye. Additionally, as shown in FIGS. 2A-2D, the arms of lid-speculum 200 have landings 205*a*, 205*b* that are sized and shaped to allow placement of a widefield camera resting on said arms of the lid speculum in a stable manner such that the speculum provides a fulcrum for movement (e.g., tilting) of camera relative to the baby eye. It is further envisioned that a camera (e.g. camera 50) resting on said lid speculum can be retro-pulsed towards the eye to provide stabilization of the eye (i.e., to prevent rotation) by causing said speculum blades to contact the sclera of the eye. It will be appreciated that the arms of the speculum can be sized (i.e., by designing the distance from the surface of the landing on which the camera is supported to surface of the blade that contacts the eye) in such a manner to place the camera at the preferred z-distance from said baby eye when the wide-field camera is pressed against the arms of said speculum 200 (i.e., so that the camera is an appropriate distance from the eye to obtain a focused image). Thus, the speculum can serve to support the widefield camera to assist with rapid positioning of camera relative to eye and maintenance of eye in a single position relative to said camera.

Each arm has a thickness T extending perpendicular to the plane in which arms 202*a* and 202*b* move and measured from an eye engagement surface 206*a*, 206*b* to an arm upper surface US that is greater than 2 mm (and typically less than 8 mm). At locations along the length of the arm, the arm upper surface having a width W in a plane parallel to the plane in which the arms move that is greater than 2 mm (and typically less than 5 mm), to support the non-contact camera. A speculum may be configured such that retraction is controlled by a spring or a thumb screw located at vertex V. In some embodiments, as shown in FIGS. 2A and 2B, each arm has a portion $P_a$, $P_b$ extending further from vertex V than its corresponding blade 204*a*, 204*b* to support a non-contact camera. Also as shown in FIGS. 2A and 2B, in some embodiments, the portion $P_a$ of first arm 202*a* that extends beyond the blade is curved toward the second arm 202*b*, and the portion $P_b$ of the second arm 202*b* that extends beyond the blade is curved toward the first arm 202*a*. Also, as shown in FIGS. 2A and 2B, each blade has a lead, end surface 207*a*, 207*b* disposed to extend under a corresponding upper or lower eyelid. The lead, end surfaces 207*a*, 207*b* move circumferentially about vertex V within an end-surface plane, and each lead end surface 207*a*, 207*b* has a normal N that extends transverse to the end-surface plane.

In some embodiments, the arm length measured from the vertex is less than 40 mm (and typically greater than 30 mm) to fit a baby eye. In some embodiments, the maximum blade spread (when not in the eye) is less than 35 mm and, in the eye, is less than 20 mm. Maximum blade spread is measured at the location of maximum separation of the blades.

In some embodiments, the arms and/or landings are not flat, but are contoured to the front surface of the camera 50 such that the interface is a lock-and-key interface to allow for precise positioning of the front surface of the camera on the speculum. The speculum can in some embodiments be placed with respect to upper and lower eyelids such that said contoured surface is centered on the cornea of the eye. When said contour of the camera 50 is applied to said contour of the lid speculum arm or arm landings, the camera would be centered with respect to the cornea of the eye as well.

Figure 3:
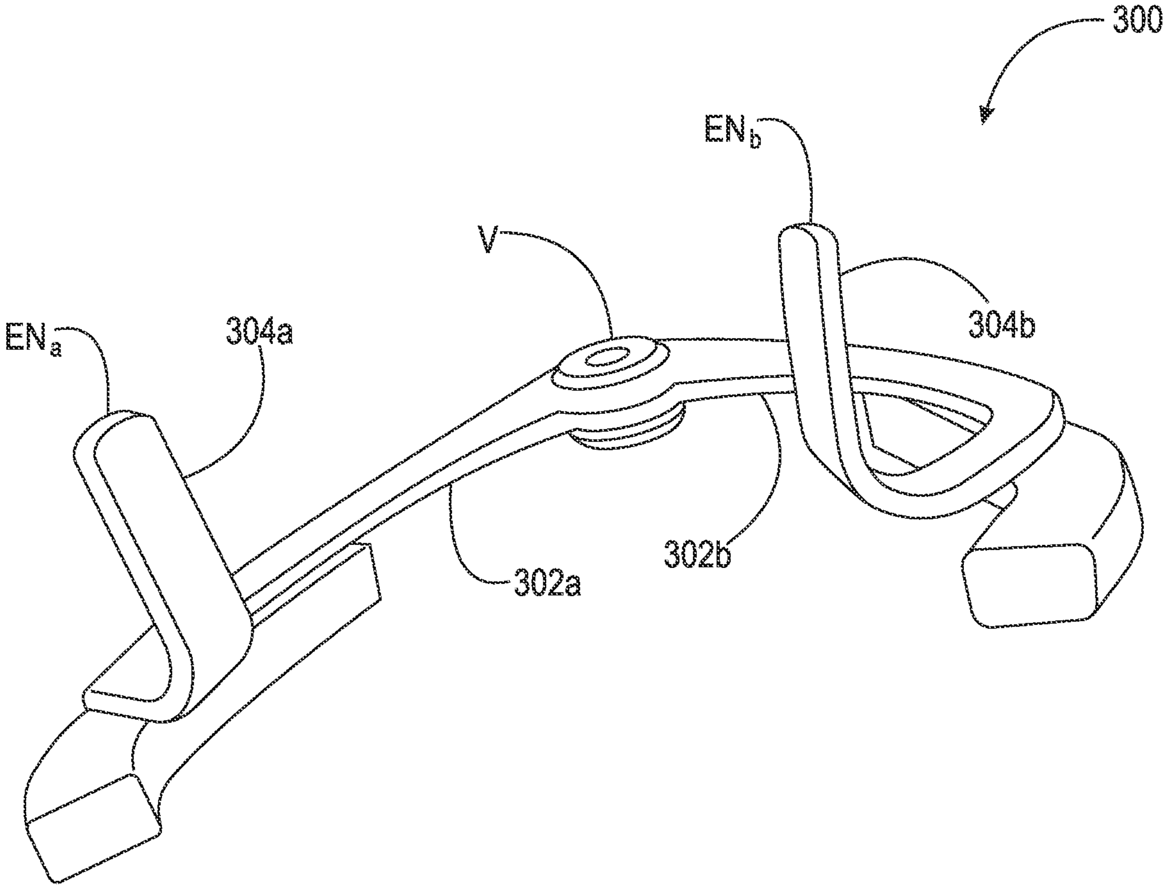
FIG. 3 is a projection view of another embodiment of a speculum according to aspects of the preset invention.

FIG. 3 is a projection view of another embodiment of a speculum 300 according to aspects of the preset invention. The blades 304*a*, 304*b* of speculum 300 have a length extending in a direction transverse to the plane in which the arms 302*a*, 302*b* move circumferentially about the vertex V, and in some embodiments substantially perpendicular to the plane. The direction in which each of the blades extends allows, the ends $EN_a$, $EN_b$ of blades (i.e., the surface of the blade most distal from arm) to press on the sclera to prevent eye rotation during imaging.

Figure 4:
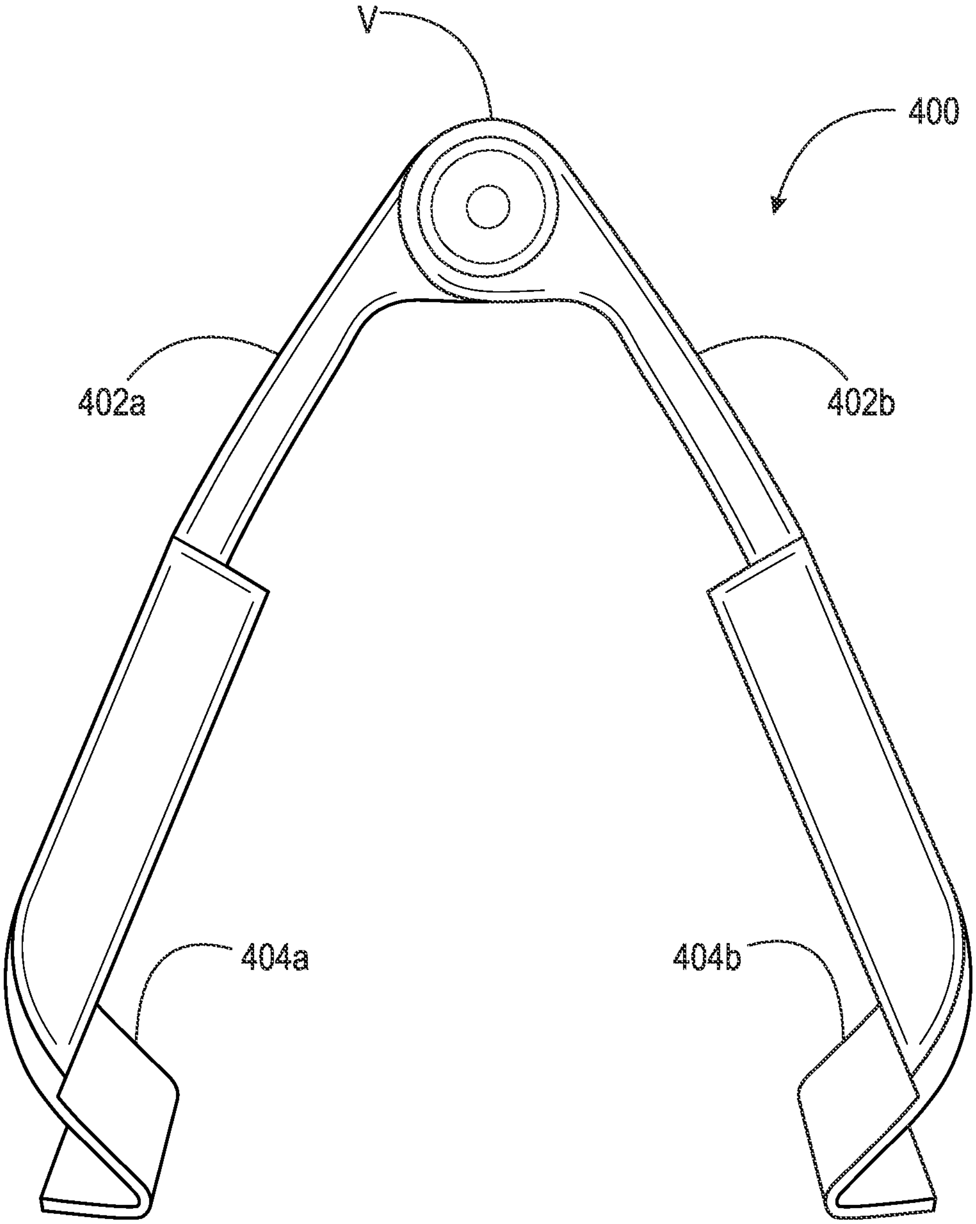
FIG. 4 is a projection view of yet another embodiment of a speculum according to aspects of the preset invention.

FIG. 4 is a projection view of yet another embodiment of a speculum 400 according to aspects of the preset invention. As shown in FIG. 4, the blades 404*a*, 404*b* may be located at the ends of the arms of the speculum (i.e., there is no portion of the arms 402*a*, 402*b* that extends beyond blades 404*a*, 404*b*, as measured from vertex V).

Figure 5A:
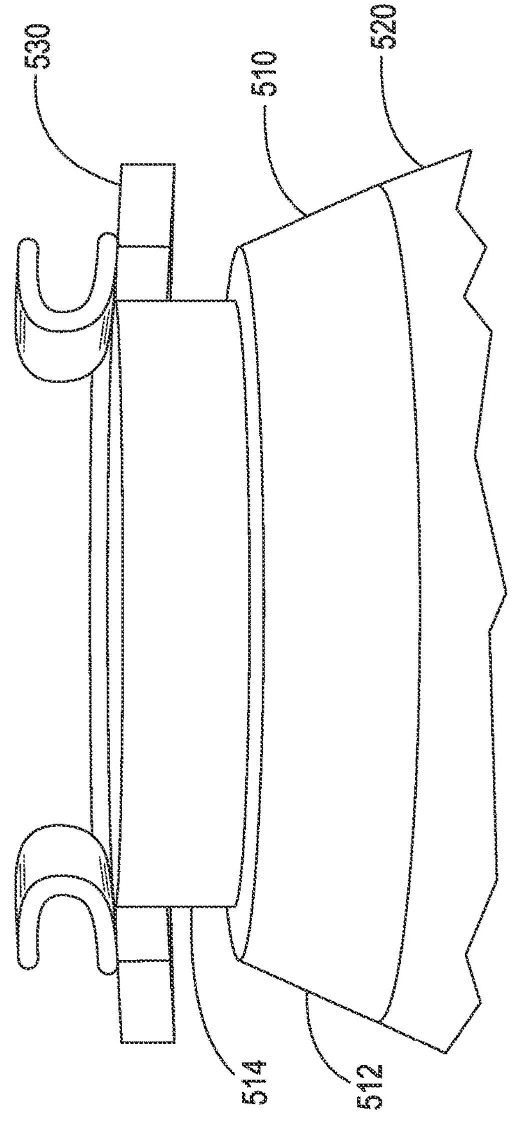
FIGS. 5A-5C are a side view, a bottom view and a top view of a combination of a spacer and a speculum used together to facilitate positioning of a camera relative to an eye.
Figure 5B:
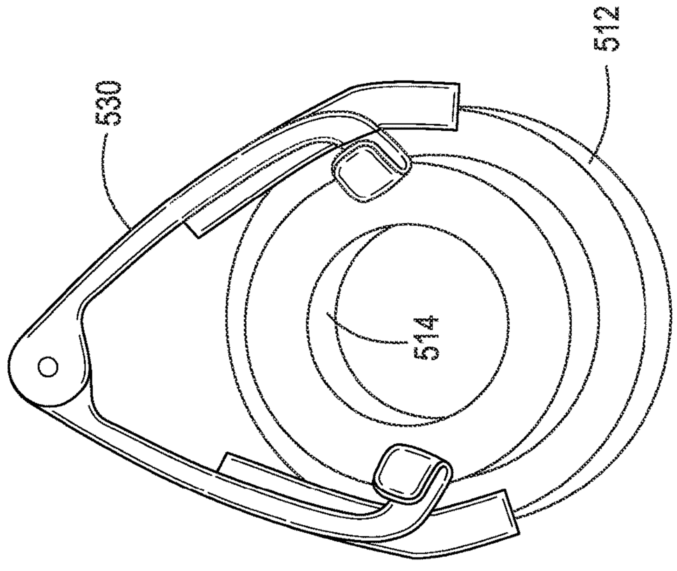
Figure 5C:
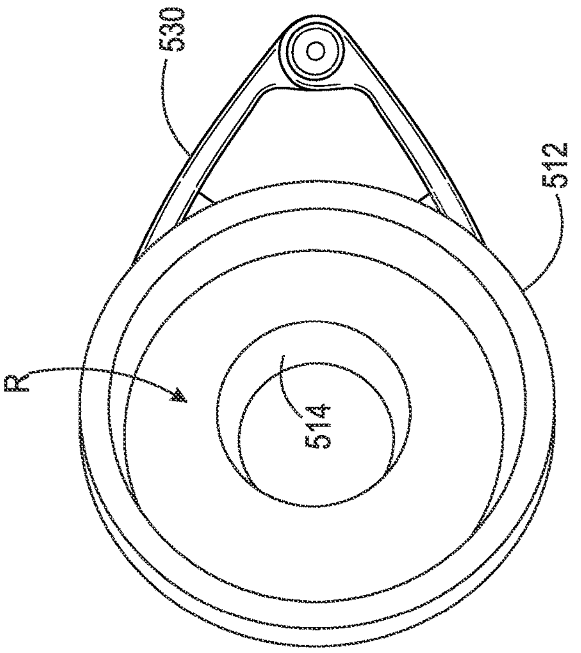
Figure 6C:
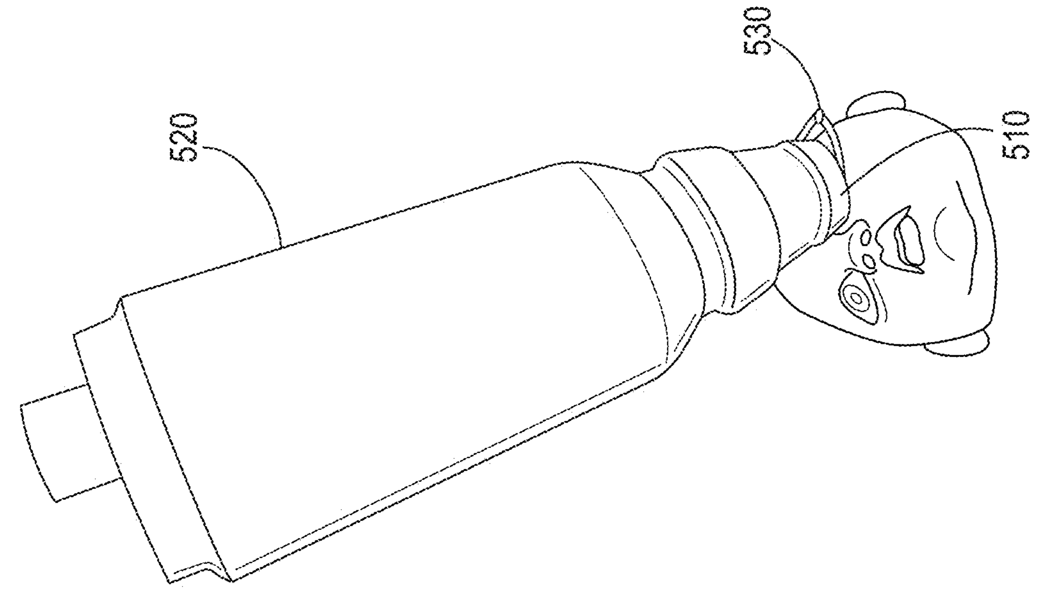
FIGS. 6A-6C show the use of a combination of a spacer and a speculum to facilitate positioning and tilting of a camera to obtain a series of images of a retina.
Figure 6B:
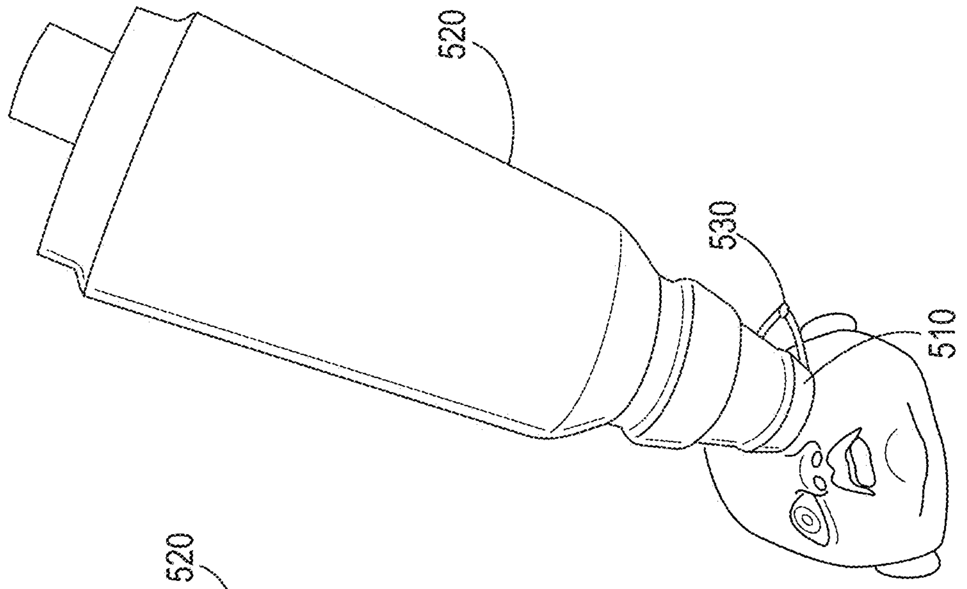
Figure 6A:
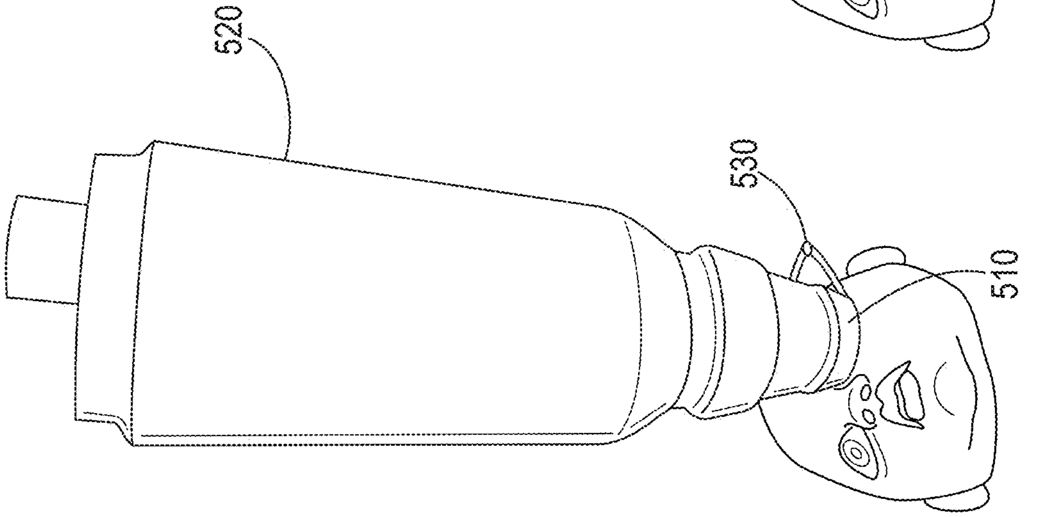

As shown in FIGS. 5A-5C, a camera spacer 510 can be introduced between a widefield camera 520 and a lid speculum 530. For example, a spacer, a camera and a speculum as described above may be used. In some embodiments, camera spacer 510 is secured to the front of camera 520 within receptacle R by sidewall 512. It is envisioned that this support (i.e., spacer 510) can provide appropriate z-distance spacing between said widefield camera 520 and said eye when resting on said lid speculum 530. Contact ring 514 of spacer 510, when used in conjunction with speculum 530, allows the spacer 510 to more readily conform to the lid speculum 530. In this embodiment the opposing surface 103*a* rests on the lid speculum landing 205*a*, 205*b*, while the contact ring 514 rests on the lid speculum blades 204*a*, 204*b*. As shown in FIGS. 6A-6C, side wall 512 of spacer 510 provides resistance against tilt of the camera relative to the central axis of said baby's eye and increase ease and precision of camera placement when capturing tilt images. In a further elaboration of this embodiment the camera spacer material is such that there is friction between the contact surface of the spacer and the lid speculum arms, landing or blades. The friction between said camera spacer material (e.g., silicon) against said lid speculum arms, landing or blades material (i.e. steel or aluminum) prevents said camera from sliding in position when tilted relative to said lid speculum or said eye.

As set forth above, implements and kits for use in imaging a fundus with a non-contact camera may be constructed and/or operated to contact an eye or not. In the embodiments described above, said implements and kits contact the sclera instead of the cornea of the eye. Contact with the sclera or other anatomical aspect of the eye other than the cornea, provides fixation of the eye relative to the camera without requiring a coupling gel between the camera and eye and without the induction of corneal striae if the amount of pressure applied by the camera is incorrect or asymmetric. It is recognized that, in these embodiments, the use of speculum or spacer to provide this contact and fixation allows for use of individual spacers and/or speculums with each eye imaged, without requiring sterilization of the camera lens surface between use on multiple eyes.

In the embodiments set forth below, implements and kits are set forth to specifically avoid contact with an imaged eye. In particular, such designs employ the surprising discovery of the inventors that, when imaging a fundus using infrared light (rather than white light), and under relevant time frames (e.g., less than 30 seconds or less than 60 seconds), substantial movement of the baby eye does not occur, thus allowing capture of images of suitable quality for diagnostic purposes, without stabilizing the eye via contact with the eye via speculum blades or a spacer.

Figure 7:
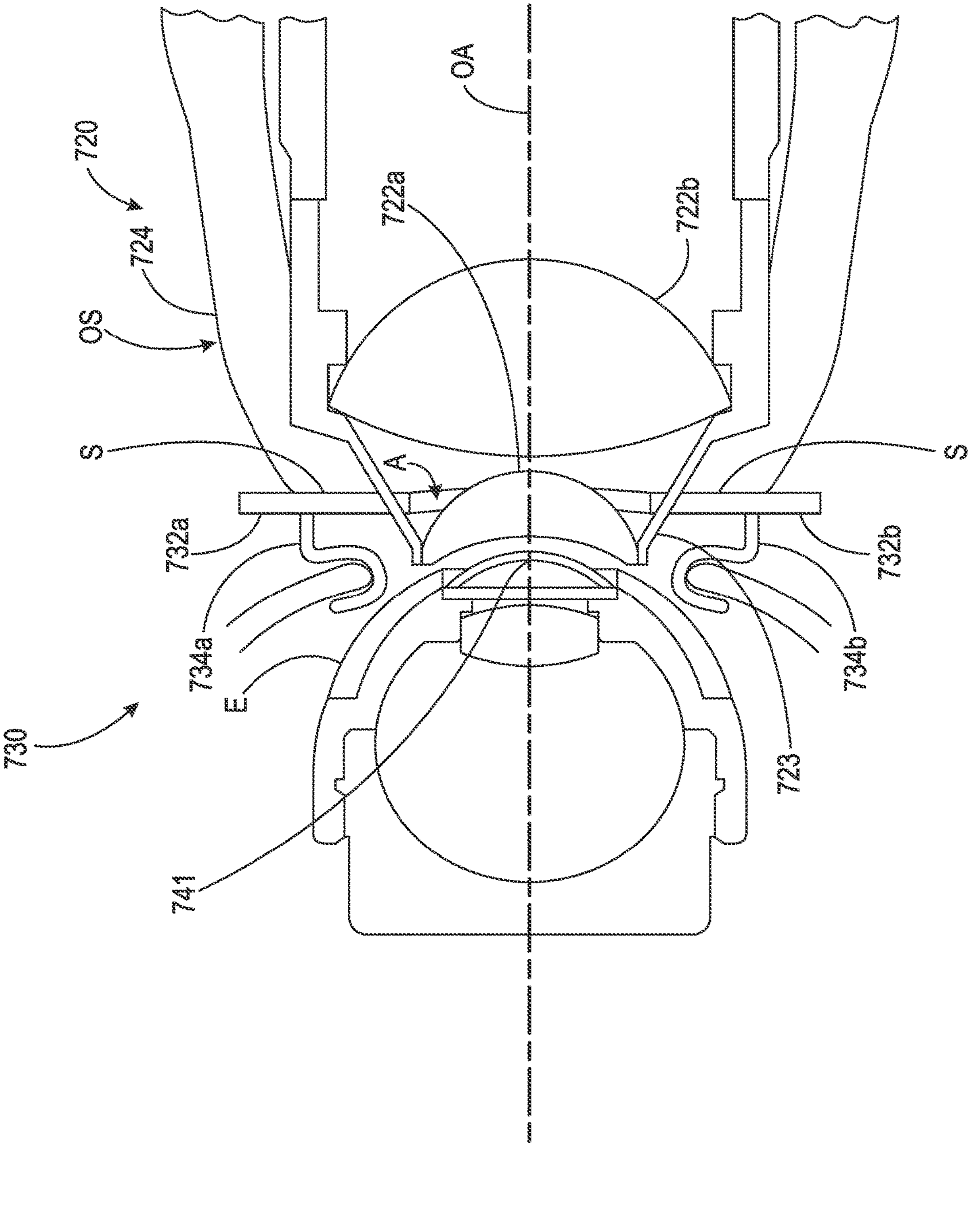
FIG. 7 is a cross sectional view of a retinal camera and a speculum arranged to facilitate retinal imaging of an eye, while avoiding contact with the imaged eye.

As shown in FIG. 7, one technique for use in imaging a fundus of an eye E includes using a speculum 730 and a fundus camera 720. The speculum comprises a first arm 732*a* having a first blade 734*a* and a second arm 732*b* having a second blade 734*b*, the first arm and the second arm coupled at a vertex V, the first blade and the second blade configured to retract an upper and lower eye lid of a patient's eye, respectively. Typically, the speculum is anchored to (and resting on) the eyelids and the eyelids are presumed a set distance (typically about 2 mm) from the eye The fundus camera comprises imaging optics 722*a*, 722*b*, contained in a lens holder 723 and/or a housing 724, housing 724 and/or the lens holder 723 having an outer surface OS containing a step S. The imaging optics image the fundus onto an image sensor 726 (shown in FIG. 9). Step S is discussed in greater detail below with reference to FIG. 9.

Referring again to FIG. 7, speculum 730 is operatively positioned relative to eye E and step S is positioned a fixed distance relative to (i.) the first arm 732*a* and the second arm 732*b* or (ii.) the first blade 734*a* and the second blade 734*b* such that the fundus camera is operatively positioned to image a fundus of an eye. In this embodiment, the blades 734*a* and 734*b* are positioned on the baby eyelid which is nominally 2 mm above the apex of the cornea 741 while the imaging optic 722*a* is positioned about 1 mm above the apex of the cornea 741 of the eye E.

As shown in FIG. 7, positioning the step S at the fixed distance may be achieved by placing the step on the (i.) the first arm 732*a* and the second arm 732*b* or (ii.) the first blade 734*a* and the second blade 734*b* (i.e., step S directly contacts the first arm 732*a* and second arm 732*b*). Also as shown in FIG. 7, lens housing 723 and one or more of imaging optics 722*a*, 722*b* (also referred to herein as a lenses) may extend beyond speculum arms 732*a*, 732*b* (i.e., closer to the eye than the arms) to allow lenses 722*a* and 722*b* to be close to eye E (e.g., within 0.5 mm of the eye). Such close positioning is typically preferred for wide-angle imaging to capture the largest field of view of the retina. While, in the illustrated embodiment, the feature on the camera housing to achieve the fixed distance is a single flat surface, the housing and speculum may have additional contour, configured such that the housing and speculum have complimentary surfaces (i.e., to form a lock-and-key interface therebetween) to establish the fixed distance and possibly a fixed rotational orientation about the optical axis OA, between the camera and the speculum. The interface may include a step on the housing.

It is to be appreciated that the imaging optics may include an objective lens 722*a* having a concave first surface (i.e., outer surface) and a biconvex second lens 722*b*; alternatively, any other suitable configuration known for obtaining a wide-field image may be used. However, an advantage of a concave outer surface is that the lens and lens holder can be configured (e.g., by having a concave curvature greater that is greater than the convex curvature of the eye) such that, when the peripheral aspect of the lens holder 723 contacts the sclera of the eye E, the lens 722*a* contained within the lens holder 723 of the camera 50, remains about 1 mm above the apex of the cornea 741 and does not directly contact the cornea.

While in this embodiment lens holder 724 is identified as a part separate from the lens housing 723, they are not required to be two individual parts. The camera housing in this embodiment does not directly contact the eye to provide a fulcrum, and instead relies on direct contact with the lid speculum to provide this fulcrum. In this manner camera 50 maintains sterility with respect to the eye.

Figure 8:
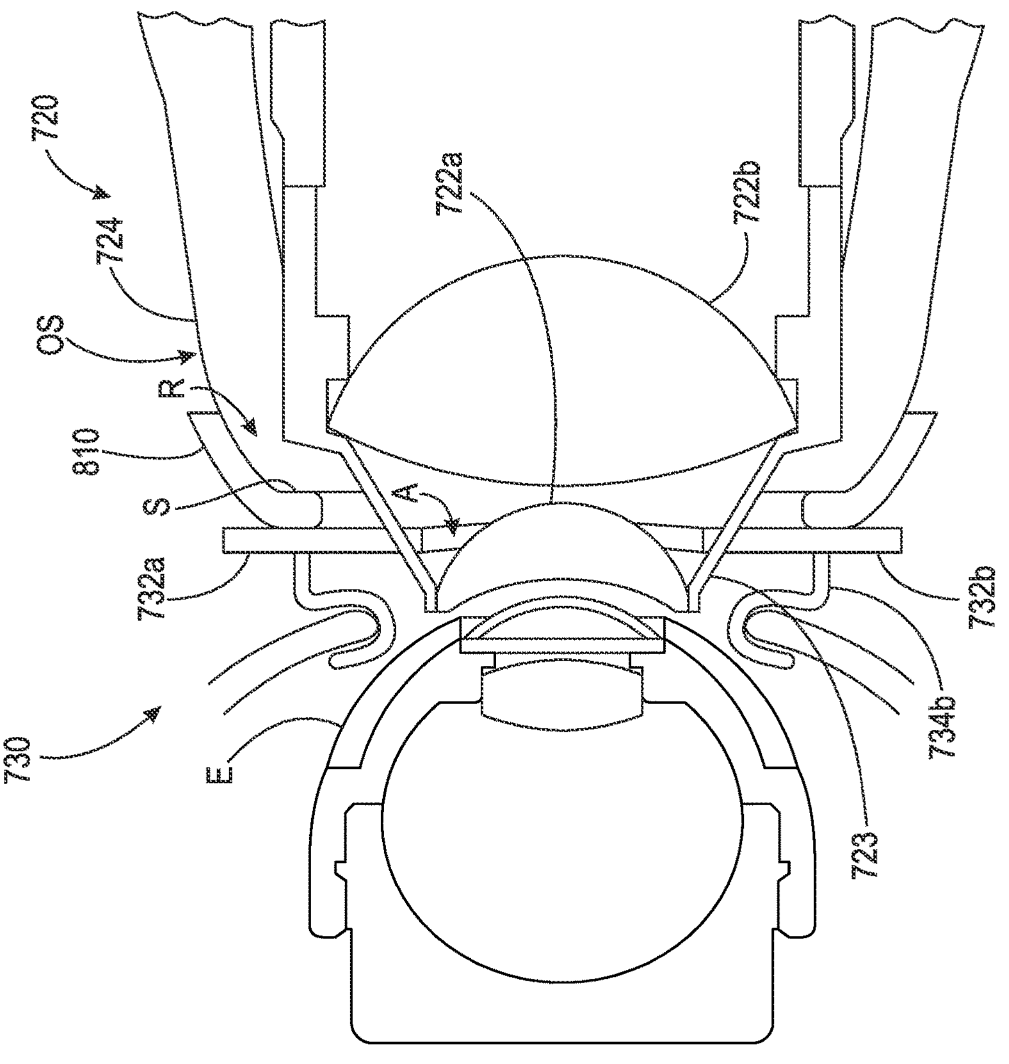
FIG. 8 is a cross sectional view of a retinal camera, a speculum and a spacer arranged to facilitate retinal imaging of an eye, while avoiding contact with the imaged eye.

Alternatively, as shown in FIG. 8, positioning of step S at the fixed distance may be achieved using a camera spacer 810 to position step S a fixed distance relative the (i.) the first arm 732*a* and the second arm 732*b* or (i.) first blade 734*a* and second blade 734*b*. Spacer 810 may be configured as any suitable spacer described above; however, a contact ring 514 may not be desirable, for example because (1) the spacer does not directly contact the eye and (2) the lens holder 723 and lens 722*a* space requirements do not permit addition of the contact ring. Spacer 810 comprises an aperture A extending therethrough (e.g., as shown in FIG. 1A), the aperture substantially centered about a longitudinal axis extending through the spacer, and the longitudinal axis to be nominally aligned with the optical axis of the camera, when the camera is operatively positioned relative the camera spacer.

In the illustrated embodiment, spacer 810 includes a spacer body with a sidewall extending from the spacer body to form a receptacle. The aperture has a diameter of 8 mm-25 mm. The spacer includes a receptacle R for receiving a portion of the camera, the receptacle terminating at an end surface including the aperture. The end surface surrounds the longitudinal axis such that, when the camera contacts the end surface, the optical axis can be aligned with the longitudinal axis. The spacer may be constructed of a semirigid material as set forth above; however other materials may be used when a wide field imaging optics used and the lens is relatively close to the eye, since such an arrangement may allow for capture of a suitable portion of the fundus without tilting of the camera. It is to be appreciated the aperture A in this embodiment would be of sufficient diameter to allow the lens holder 723 to pass through the aperture. It is to be further appreciated that, in this embodiment, the spacer is only in contact with the lens housing 724; however, other configurations are possible. It is yet further appreciated that lens holder 723 and lens 722*a* are positioned at a closer distance to the eye E than the arms of the lid speculum 732*a*, 732*b*. The thickness of the spacer 810 can be chosen to allow sub millimeter non-contact positioning of the lens holder and the lenses with respect to the apex of the cornea of the eye without requiring direct contact with the cornea. While, in the illustrated embodiment, the feature on the camera housing to achieve the fixed distance is a single flat surface, the housing and spacer may have additional contour, configured such that the housing and spacer have complimentary surfaces (i.e., to form a lock-and-key interface therebetween) to establish the fixed distance and possibly a fixed rotational orientation about the optical axis OA, between the camera and the spacer. The interface may include a step on the housing.

Figure 9A:
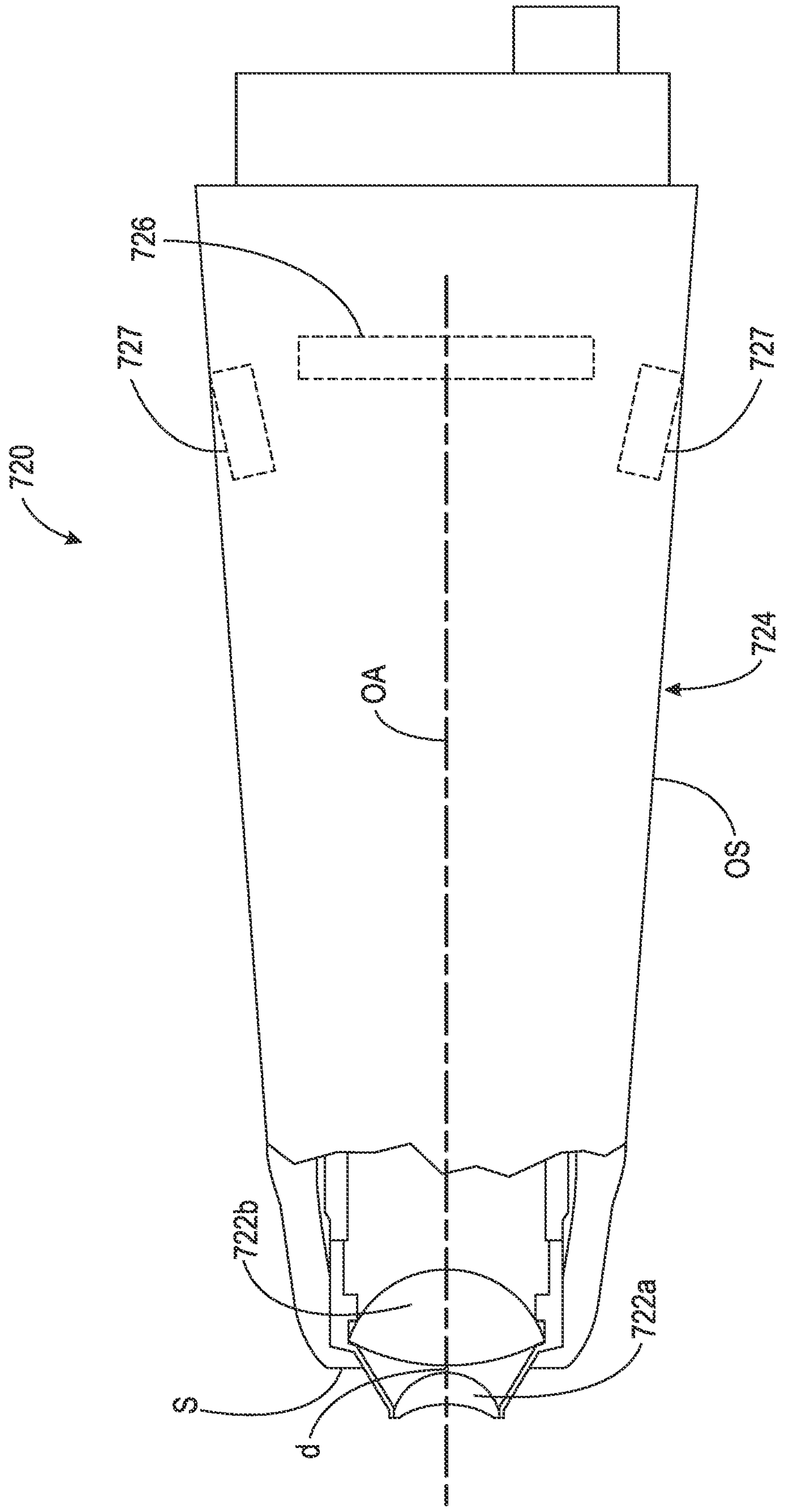
FIG. 9A is a cross sectional view of a retinal camera shown in FIGS. 7 and 8.

FIG. 9A shows fundus camera 720 apart from other implements and the eye. As illustrated, camera 720 comprises a housing 724 having an outer surface OS containing at least one step S. The fundus camera comprises imaging optics 722*a* and 722*b* contained in a lens housing 723, and having an optical axis OA. The housing encloses the imaging optics and an image sensor 726 which captures fundus images produced by the imaging optics. The at least one step extends transverse to the optic axis. As indicated above, the purpose of the at least one step S is to interface with first and second arms of a speculum 730 (shown in FIG. 7) or with spacer 810 (shown in FIG. 8) to maintain the imaging optics at an appropriate distance from an eye so as to permit imaging of the eye's fundus. The at least one step may be a single step extending completely around the optical axis to form the interfaces with the arms or spacer, or may be formed as two or more separate steps, each extending a limited angular distance around the optical axis. If two or more steps are present, they are typically formed at a common location d along the optical axis.

The step comprises a flat surface for interfacing with an arm of a speculum or a spacer. Typically, the at least one step extends substantially perpendicular to the optical axis (i.e., within about +/−10 degrees of perpendicular); however, the primary objective of the step and arm/spacer interface is to maintain the imaging optics at an appropriate distance from an eye and steps extending at another angle are possible, provided that the speculum or spacer has an suitable interface surface. It is further appreciated that the at least one step may have additional contour that is not flat configured to interface with the speculum or spacer (e.g., a lock and key interface) to secure close apposition between the camera and the speculum and/or spacer. One or more infrared light sources 727 are provided to illuminate an eye during imaging. For example, illumination and/or image processing techniques as described in U.S. Pat. No. 10,925,486 to Yates, et al. may be used.

Figure 9B:
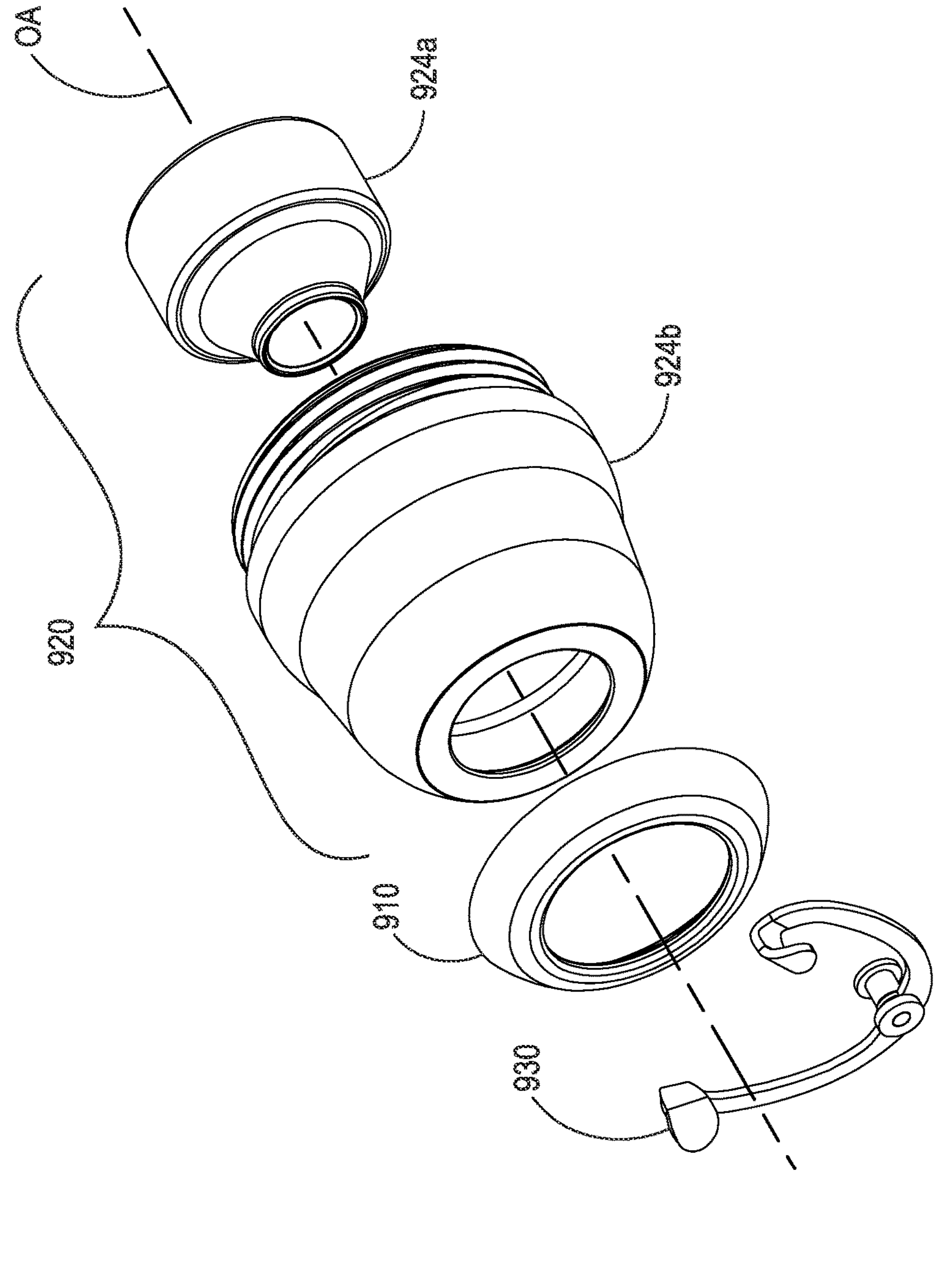
FIG. 9B is a projection view of a front portion of an example of a camera according to aspects of the present invention.
Figure 10:
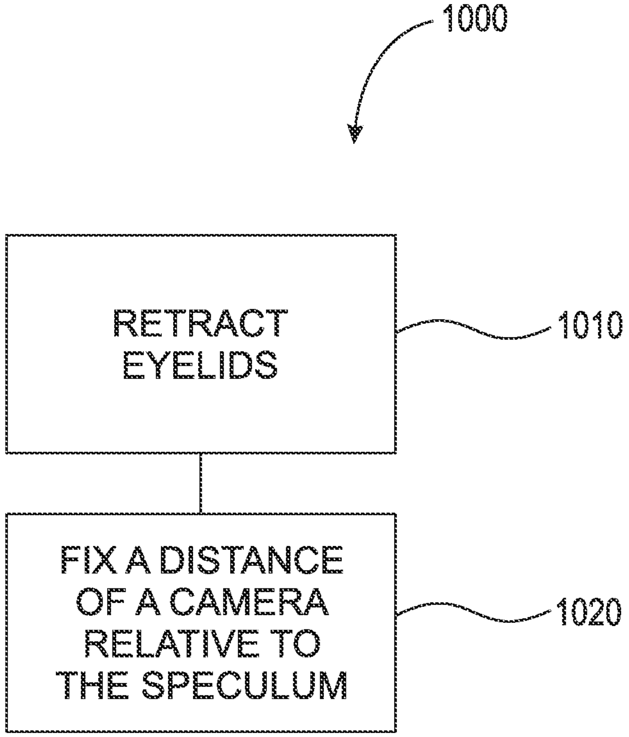
FIG. 10 is a flowchart illustrating an example of a method of operatively positioning a camera to image a fundus of the eye.

FIG. 9B is a projection view of an example of a camera 920, along with a spacer 910 and a speculum 930 all according to aspects of the present invention. The camera, spacer and speculum are separated along optical axis OA to facilitate viewing of the components. In the illustrated embodiment, optics 722*a*, 722*b* (shown in FIG. 9A) are contained within a lens housing 924*a*. In the illustrated embodiment, the lens housing fits within a front portion 924*b* of the main camera housing which is coupled to a back portion (not show) of the main camera housing that includes the image sensor 726 and other components. The front portion 924*b*, the back portion combine with optical housing 924*a* to form outer surface OS. Such a design, while advantageous in some instances, is only one option for a housing design.

As indicated above, aspects of the invention include operation of implements to avoid contact with an eye while imaging the eye's fundus. In particular, such aspects include a method of positioning a non-contact, widefield camera having an optical axis relative to an eye. An example of a method 1000 according to aspects of the invention comprises the following steps.

At step 1010, an upper eye lid and a lower eye lid of a patient's eye are retracted using a first blade and a second blade of a speculum, respectively. The first blade extends from a first arm of the speculum and the second blade extends from a second arm of the speculum.

At step 1020, fixing a distance of a step the camera relative to (i.) the first arm and the second arm or (ii.) the first blade and the second blade.

As a result of the above steps, the camera is operatively positioned to image a fundus of the eye onto a sensor of the camera, and the images can be obtained by activating the camera.

As discussed with reference to FIG. 7, fixing a distance of the camera may be achieved by contacting (i.) the first arm and the second arm or (ii.) the first blade and the second blade with the camera. Alternatively, as discussed with reference to FIG. 8, fixing a distance of the camera may be achieved by positioning a spacer on (i.) the first arm and the second arm or (ii.) the first blade and the second blade, the spacer having an aperture extending therethrough and a longitudinal axis extending through the aperture. Typically, the camera is located 1 to 10 mm from a surface of the eye in the direction of the longitudinal axis, for example to allow a wide angle image to obtained through the pupil.

Although various embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A kit for use in imaging a fundus of an eye, comprising:

A. a speculum comprising a first arm having a first blade and a second arm having a second blade, the first arm and the second arm coupled at a vertex, the first blade and the second blade configured to retract an upper and lower eye lid of the eye, respectively;

B. a fundus camera comprising imaging optics and a housing and characterized by an optical axis, the housing containing the imaging optics and having an outer surface; and C. a camera spacer, comprising (I) a spacer body having an aperture extending therethrough, the aperture substantially centered about a longitudinal axis of the spacer, (II) a contact ring connected to a distal end of the spacer body and having a contact surface at a distal end and (III) a receptacle formed by a sidewall extending from a proximal end of the spacer body, for receiving a portion of the camera, whereby, when (i) the speculum is operatively positioned relative to the eye, (ii) the camera is disposed in the receptacle and (iii) the contact surface contacts the (a) the first arm and the second arm or (b) the first blade and the second blade, the optical axis and the longitudinal axis extend in a same direction such that the fundus camera is operatively positioned to image a fundus of the eye.

2. The kit of claim 1, wherein the kit is configured to form an interface between the sidewall and the outer surface of the camera, the interface being a lock and key interface.

3. The kit of claim 1, wherein the camera comprises an objective lens having a concave first surface.

4. The kit of claim 1, wherein the spacer is constructed of a semirigid material.

* * * * *